US006664415B2

(12) United States Patent
Brahm et al.

(10) Patent No.: US 6,664,415 B2
(45) Date of Patent: Dec. 16, 2003

(54) PROCESS FOR PREPARING ORGANIC MONOISOCYANATES

(75) Inventors: Martin Brahm, Odenthal (DE); Lutz Schmalstieg, Köln (DE); Ulrich Geron, Plaidt (DE); Hans-Günter Behr, Leverkusen (DE); Jörg Morawski, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 23 days.

(21) Appl. No.: 09/845,873

(22) Filed: Apr. 30, 2001

(65) Prior Publication Data

US 2001/0041810 A1 Nov. 15, 2001

(30) Foreign Application Priority Data

May 4, 2000 (DE) .......................................... 100 21 742

(51) Int. Cl.$^7$ ............................................. C07C 263/00
(52) U.S. Cl. ...................... 560/350; 560/338; 560/344; 560/352
(58) Field of Search ................................. 560/338, 344, 560/352, 350

(56) References Cited

U.S. PATENT DOCUMENTS

| 2,611,782 | A | * | 10/1952 | Bortnick | |
|---|---|---|---|---|---|
| 3,379,749 | A | * | 4/1968 | Hennig et al. | |
| 4,223,145 | A | * | 9/1980 | Hentschel et al. | |
| 4,870,198 | A | | 9/1989 | Mormann et al. | .......... 307/414 |
| 4,886,902 | A | | 12/1989 | Mormann et al. | .......... 307/106 |
| 4,946,990 | A | | 8/1990 | Mormann et al. | .......... 307/106 |

FOREIGN PATENT DOCUMENTS

EP 341515 11/1989

OTHER PUBLICATIONS

Synthesis, 12, (month unavailable) 1988, pp. 990–991, Werner Mormann et al, "Eine einfache und vielseitige Synthese von trimethylsiloxy–substituierten Isocyanaten".
Angew. Chem, 72, No. 24, (month unavailable) 1960, p. 1002, von Dr. W. Bunge, "Einfache Laboratoriumsmethode zur Herstellung niedrigsiedender Isocyanate".
Sieken, Annalen der Chemie, 562, (month unavailable) 1949, p. 81, Siefken.

* cited by examiner

Primary Examiner—Johann Richter
Assistant Examiner—Paul A. Zucker
(74) Attorney, Agent, or Firm—Joseph C. Gil; Thomas W. Roy

(57) ABSTRACT

The present invention relates to a process for preparing a low boiling monoisocyanate having a boiling point of between 70 and 320° C. at standard pressure by reacting A) a high boiling isocyanate compound having a boiling point of at least 180° C. at standard pressure and an HC content of at least 50 ppm with B) a monoamine having a primary amino group, at a maximum reaction temperature of 180° C. and a molar ratio of isocyanate groups to amino groups of at least 4:1 to form a compound containing a biuret/urea group, simultaneously thermally decomposing this compound in situ to form a monoisocyanate corresponding to monoamine B) and removing the monoisocyanate by distillation, optionally under vacuum.

14 Claims, No Drawings

PROCESS FOR PREPARING ORGANIC MONOISOCYANATES

BACKGROUND OF THE INVENTION

1. Field of the Invention

The present invention relates to a phosgene-free process for preparing organic monoisocyanates by thermally decomposing compounds containing biuret/urea groups and prepared in situ by the reaction of isocyanate compounds and primary monoamines.

2. Description of the Prior Art

The preparation of organic isocyanate compounds with phosgene is well known and described in numerous publications and patents (for example Houben-Weyl, Methoden der organischen Chemie [Organic Chemistry Methods], Vol. 8, p. 120 et seq. (Georg Thieme Verlag Stuttgart 1952)). Special techniques and costly production and safety systems are a prerequisite for the safe handling of phosgene. For this reason there has been no shortage of attempts to synthesize isocyanate compounds by phosgene-free methods.

One simple laboratory method which is known for the phosgene-free preparation of isocyanates is a thermal decomposition of compounds having biuret or urea structures. A low molecular weight amine or polyamine is incorporated into an excess of a high boiling isocyanate compound, and the low boiling isocyanate formed in an equilibrium reaction is removed by distillation at temperatures of 200° C. and above. The publication Bunge, W., Angew. Chem. 72, 1002 (1960) gives details of this "Simple laboratory method for the preparation of low boiling isocyanates". The publication Siefken, Annalen der Chemie 562, 81 (1949) also outlines this method with temperatures greater than 200° C. being described. Patent application EP-A 307 756 and the publication W. Mormann, G. Leukel, Synthesis 12, 990 et seq. (1988) optimize the principle of this method for special siloxyisocyanates.

For numerous reasons it is difficult to optimize the processes mentioned. For example, at temperatures of 200° and above polyisocyanates react in a manner no longer controllable and sometimes with evolution of gas, to form high molecular weight secondary products, such that at these high temperatures unpredictable reaction processes may occur in an industrial process.

There is little possibility of removing the high molecular weight secondary products from the reaction vessel on an industrial scale because the viscosity is too high. For reasons of viscosity it is not possible industrially to react equimolar quantities of high boiling polyisocyanates and low boiling amines, such as described in EP-A 307 756.

An object of the present invention is to provide a phosgene-free process for the preparation of monoisocyanates, which has broad applicability and can be carried out effectively, especially on a large industrial scale.

This object may be achieved with the process according to the invention, which is described in greater detail hereinafter.

SUMMARY OF THE INVENTION

The present invention relates to a process for preparing a low boiling monoisocyanate having a boiling point of between 70 and 320° C. at standard pressure by reacting A) a high boiling isocyanate compound having a boiling point of at least 180° C. at standard pressure and an HC content of at least 50 ppm with B) a monoamine having a primary amino group, at a maximum reaction temperature of 180° C. and a molar ratio of isocyanate groups to amino groups of at least 4:1 to form a compound containing a biuretlurea group, simultaneously thermally decomposing this compound in situ to form a monoisocyanate corresponding to monoamine B) and removing the monoisocyanate by distillation, optionally under vacuum.

DETAILED DESCRIPTION OF THE INVENTION

High boiling isocyanate compounds A) are compounds and mixtures having isocyanate groups and boiling points of above 180° C., preferably above 250° C. and more preferably above 300° C. under standard conditions.

Under the reaction conditions the boiling temperature of isocyanate component A) must be at least 10° C., preferably 20° C. and more preferably 40° C. above the adjusted reaction temperature.

Suitable isocyanate compounds A) are known and include compounds having aliphatically, cycloaliphatically, araliphatically or aromatically bound isocyanate groups. Examples include monoisocyanates such as stearyl isocyanate and naphthyl isocyanate; diisocyanates such as 1,4-diisocyanatobutane, 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis(isocyanatomethyl)cyclohexane, 1-isocyanato-3,3,5-trimethyl-5-isocyanatomethyl cyclohexane (isophorone diisocyanate, IPDI), 4,4'-diisocyanatodicyclohexyl methane, 1-isocyanato-1-methyl-4(3)-isocyanatomethyl cyclohexane (IMCI), bis(isocyanatomethyl)norbornane, 2,4- and/or 2,6-diisocyanatotoluene (TDI), 2,4'- and/or 4,4'-diisocyanatodiphenylmethane and higher homologs, 1,5-diisocyanatonapbthalene and dipropylene glycol diisocyanate; triisocyanates and/or higher functional isocyanates such as 4-isocyanatomethyl-1,8-octane diisocyanate (nonane truisocyanate), 1,6,11-undecane triisocyanate; and mixtures of these isocyanate compounds.

Modified isocyanate compounds prepared from the preceding diisocyanates and triisocyanates by oligomerization reactions, such as trimerization, are also usable. Mixtures of the modified and unmodified isocyanates may also be used.

Compounds containing aromatically bound isocyanate groups are preferably used. Polyisocyanates of the diphenylmethane series having a bicyclic content (total of 2,2-, 2,4- and 4,4-diphenylmethane diisocyanate) of at least 85 wt. %, based on the total weight of the isocyanate component A), are preferably used as the isocyanate component A).

It is essential that the isocyanate component A) has an HC content (hydrolyzable chlorine compounds content) of at least 50 ppm, preferably at least 150 ppm and more preferably at least 300 ppm. This can be ensured either by an existing sufficiently high chlorine content of the isocyanate component A) due to its method of preparation, or by the addition of compounds which contain hydrolyzable chlorine. Examples of such compounds are benzoyl chloride, terephthaloyl dichloride and isophthaloyl chloride. The hydrolyzable chlorine content of the isocyanate component A) may be determined by known methods.

Any aliphatic, cycloaliphatic or aromatic compounds having a primary amino group and where the monoisocyanates forming as reaction products can be removed by distillation from the reaction mixture under the reaction conditions, may be used as low molecular weight monoamines B). The monoamines may contain, in addition to the amino group, other functional groups that are inert to isocyanate groups under the reaction conditions. The monoamines may be directly used at the purity available industrially without special purification.

Examples of suitable monoamines include $C_3$–$C_{18}$-alkylamines such as the isomeric butylamines, pentylamines, hexylamines, heptylamines, octylamines, nonylamines, decylamines and dodecylamines; $C_3$–$C_{18}$-alkylene amines such as alkylamine; monoamines based on optionally unsaturated, long-chain fatty acids; $C_5$–$C_{18}$-cycloalkylamines such as cyclohexylamine; aromatic amines such as phenylamine, ortho- and parafluorophenylamine, ortho- and para-chlorophenylamine and naphthylamine; alkyl phenylamines; and alkyl phenylamines containing halogen atoms. The carbon chains of the amines may be contain oxygen and/or sulfur atoms in the form of ether or thioether groups.

Monoamines containing an aromatically bound amino group are preferably used. Anilines containing halogen are especially preferred.

Monoisocyanates C) prepared according to the invention are derived from monoamines B) and must be distillable under the specified reaction conditions. They have a boiling point of at least 70° C., preferably at least 110° C. and at most 320° C., preferably at most 240° C., at standard pressure. The molecular weight of these monoisocyanates is generally 83 to 270.

In the process according to the invention high boiling isocyanate component A) and monoamine component B) are reacted at a molar ratio of isocyanate groups to primary amino groups of at least 4:1, preferably 5:1 to 20:1 and more preferably from 6:1 to 8:1, and at a maximum temperature of 180° C., preferably 80° C. to 160° C. and more preferably 120° C. to 140° C. Monoamine component B) may be incorporated in pure form or in a blend with other non-reactive compounds. The monoamine is preferably incorporated as a solution in a solvent that does not boil under the process conditions. The solution preferably has a concentration of 10 to 90%, more preferably 40 to 60%. Examples of suitable solvents include high boiling trialkyl phosphates or tritoluyl phosphates.

The reaction temperature and bottom temperature in the reaction vessel is limited to a maximum of 180° C. Working is preferably at reaction temperatures of from 100° C. to 170° C. and particularly preferably from 120° C. to 160° C.

The removal by distillation of monoisocyanate C) may take place under ambient pressure or at reduced pressure, preferably at reduced pressure and more preferably at a pressure of 5 to 200 mbar.

The process according to the invention enables monoisocyanates to be industrially prepared simply and at yields of over 70%. The bottom product that forms may be handled without difficulty.

The purity of monoisocyanates C) is preferably over 90%, more preferably over 99%. Therefore, monoisocyanate C) may be used directly in modification reactions and as intermediates without further purification.

The invention is further illustrated but is not intended to be limited by the following examples in which all parts and percentages are by weight unless otherwise specified.

EXAMPLES

The hydrolyzable chlorine content was determined by potentiometric titration. Methanol was added to the sample for analysis and the urethane reaction was carried out under reflux for 10 minutes. After dilution with water, the resulting mixture was then hydrolyzed by boiling under reflux. After acidification with nitric acid and addition of a known amount of sodium chloride, the ionic chlorine formed was titrated argentometrically with a silver nitrate standard solution. The titration was carried out with incremental reagent addition and automatic end point evaluation with drift control (equilibrium titration).

Example 1

(According to the Invention)

420 kg of a technical grade polyisocyanate of the diphenylmethane series having a bicyclic content of 90 wt. % (Desmodur MDI 90/10, commercial product of Bayer AG, NCO content 32%, viscosity 13 mPa·s, HC content 357 ppm, determined potentiometrically) were drawn under vacuum at room temperature into a reaction vessel with a distillation unit, and were heated to 130° C. after purging with nitrogen.

At this temperature 53.7 kg of n-hexylamine were incorporated from a supply into the reactor such that the reactor internal temperature did not rise above 150° C. (clearly exothermic reaction, cooling essential).

When the hexylamine addition was finished the boiler internal temperature was adjusted to 160° C., and careful evacuation took place until a reflux was clearly observed. The reflux divider of the distillation unit was then adjusted to 5 parts take-off and 1 part reflux. The hexyl isocyanate that formed was distilled off.

Based on the amount of distillate formed, the boiler internal pressure was carefully reduced to 20 mbar during the distillation. Towards the end of the distillation the reflux ratio was adjusted to full take-off.

After approx. 10 hours the reaction/distillation was complete, and after purging with nitrogen, the bottom product was cooled to 120° C. At this temperature the bottom still flowed well and was removed by the application of a slight over-pressure and filled into containers.

Yield: 87% of theoretical

NCO content: 33.1%

Appearance: clear, colorless fluid n-hexyl isocyanate content: 99.4% (determined by GC)

Example 2

Comparison 2,100 g of 4,4'-diisocyanatodiphenylmethane (HC content<10 ppm, determined potentiometrically) were charged into a 4,000 ml four-necked flask (equipped with a stirrer, internal thermometer and distillation bridge), melted and heated to approx. 130° C. At this temperature 270 g of n-hexylamine were incorporated. The temperature increased to 160° C.

When the addition was finished careful evacuation took place, and the monoisocyanate obtained was removed by distillation. The reaction temperature was increased to 190 to 195° C. After a reaction time of 5 hours the reaction batch was so highly viscous that it could not be removed from the four-necked flask. Despite these severe conditions the yield of hexyl isocyanate removed by distillation was 83%, which is less than the production trial (see Example 1). The reaction flask could not be cleaned after the trial was over and was discarded with its contents.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a low boiling monoisocyanate having a boiling point of between 70 and 320° C. at standard pressure by reacting A) a high boiling isocyanate compound having a boiling point of at least 180° C. at standard pressure and an HC content of at least 50 ppm with B) a monoamine having a primary amino group and comprising a $C_3$–$C_{18}$-alkyamine, a $C_3$–$C_{18}$-alkylene amine, a $C_5$–$C_{18}$-cycloalkyl amine, or an aromatic amine, provided that the monoamine only contains oxygen and/or sulfur as heteroatoms, at a maximum reaction temperature of 180° C. and a molar ratio of isocyanate groups to amino groups of at least 4:1 to form a compound containing a biuret/urea group, simultaneously thermally decomposing this compound in situ to form a monoisocyanate corresponding to monoamine B) and removing the monoisocyanate by distillation, optionally under vacuum.

2. The process of claim 1 wherein isocyanate component A) has an HC content of at least 300 ppm and the maximum reaction temperature is 160° C.

3. The process of claim 1 wherein monoamine B) comprises an aromatic monoamine.

4. The process of claim 2 wherein monoamine B) comprises an aromatic monoamine.

5. The process of claim 1 wherein isocyanate compound A) contain aromatically bound isocyanate groups.

6. The process of claim 2 wherein isocyanate compound A) contain aromatically bound isocyanate groups.

7. The process of claim 3 wherein isocyanate compound A) contain aromatically bound isocyanate groups.

8. The process of claim 4 wherein isocyanate compound A) contain aromatically bound isocyanate groups.

9. A process for preparing a low boiling monoisocyanate having a boiling point of between 70 and 320° C. at standard pressure by reacting A) a high boiling isocyanate compound having a boiling point of at least 180° C. at standard pressure and an HC content of at least 50 ppm with B) a monoamine having a primary amino group, at a maximum reaction temperature of 170° C. and a molar ratio of isocyanate groups to amino groups of at least 4:1 to form a compound containing a biuret/urea group, simultaneously thermally decomposing this compound in situ to form a monoisocyanate corresponding to monoamine B) and removing the monoisocyanate by distillation, optionally under vacuum.

10. The process of claim 9 wherein isocyanate component A) has an HC content of at least 300 ppm and the maximum reaction temperature is 160° C.

11. The process of claim 9 wherein monoamine B) comprises an aromatic monoamine.

12. The process of claim 9 wherein isocyanate compound A) contains aromatically bound isocyanate groups.

13. The process of claim 10 wherein isocyanate compound A) contains aromatically bound isocyanate groups.

14. The process of claim 11 wherein isocyanate compound A) contains aromatically bound isocyanate groups.

* * * * *